(12) United States Patent
Hamer et al.

(10) Patent No.: US 8,551,157 B2
(45) Date of Patent: Oct. 8, 2013

(54) ENDOLUMINAL PROSTHETIC CONDUIT SYSTEMS AND METHOD OF COUPLING

(75) Inventors: Rochelle M. Hamer, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 12/895,549

(22) Filed: Sep. 30, 2010

(65) Prior Publication Data

US 2011/0022154 A1   Jan. 27, 2011

Related U.S. Application Data

(63) Continuation of application No. 11/835,789, filed on Aug. 8, 2007, now abandoned.

(51) Int. Cl.
  *A61F 2/82* (2013.01)
(52) U.S. Cl.
  USPC ........................................................ 623/1.35
(58) Field of Classification Search
  USPC .............................................. 623/1.35–1.38
  See application file for complete search history.

(56) References Cited

U.S. PATENT DOCUMENTS

| 3,774,615 | A | 11/1973 | Lim et al. |
| 3,818,515 | A | 6/1974 | Neville |
| 4,728,328 | A | 3/1988 | Hughes et al. |
| 6,042,605 | A | 3/2000 | Martin et al. |
| 6,210,429 | B1 * | 4/2001 | Vardi et al. ................... 623/1.11 |
| 6,352,561 | B1 | 3/2002 | Leopold et al. |
| 6,361,637 | B2 | 3/2002 | Martin et al. |
| 6,520,986 | B2 | 2/2003 | Martin et al. |
| 6,551,350 | B1 | 4/2003 | Thornton et al. |
| 6,645,242 | B1 * | 11/2003 | Quinn ........................ 623/1.16 |
| 6,890,349 | B2 | 5/2005 | McGuckin, Jr. et al. |
| 6,949,121 | B1 * | 9/2005 | Laguna ....................... 623/1.35 |
| 7,537,609 | B2 * | 5/2009 | Davidson et al. ............ 623/1.35 |
| 7,550,004 | B2 | 6/2009 | Bahler et al. |
| 7,828,837 | B2 * | 11/2010 | Khoury ....................... 623/1.35 |
| 8,021,412 | B2 * | 9/2011 | Hartley et al. ............... 623/1.13 |
| 8,052,736 | B2 * | 11/2011 | Doig et al. ................... 623/1.15 |
| 2002/0042650 | A1 * | 4/2002 | Vardi et al. .................. 623/1.35 |
| 2005/0222668 | A1 | 10/2005 | Schaeffer et al. |
| 2006/0247761 | A1 | 11/2006 | Greenberg et al. |
| 2007/0055363 | A1 | 3/2007 | Chuter et al. |
| 2007/0179592 | A1 * | 8/2007 | Schaeffer .................... 623/1.35 |
| 2008/0269866 | A1 * | 10/2008 | Hamer et al. ................ 623/1.11 |
| 2009/0043376 | A1 * | 2/2009 | Hamer et al. ................ 623/1.35 |

FOREIGN PATENT DOCUMENTS

WO   2004/016193   2/2004

* cited by examiner

*Primary Examiner* — Suzette J Gherbi
(74) *Attorney, Agent, or Firm* — Gilbert R. Gabo

(57) ABSTRACT

A modular prosthetic conduit system such as a stent or stent graft system tailored for the repair of aneurysms or other compromised vessel walls. The stent or stent graft system incorporates various means to interlock the multiple modular components used in the repair procedure. The present invention further provides a modular stent graft system tailored for the repair of aneurysms or other compromised vessel walls that cross or are adjacent to a branch or bifurcation in a vessel.

31 Claims, 16 Drawing Sheets

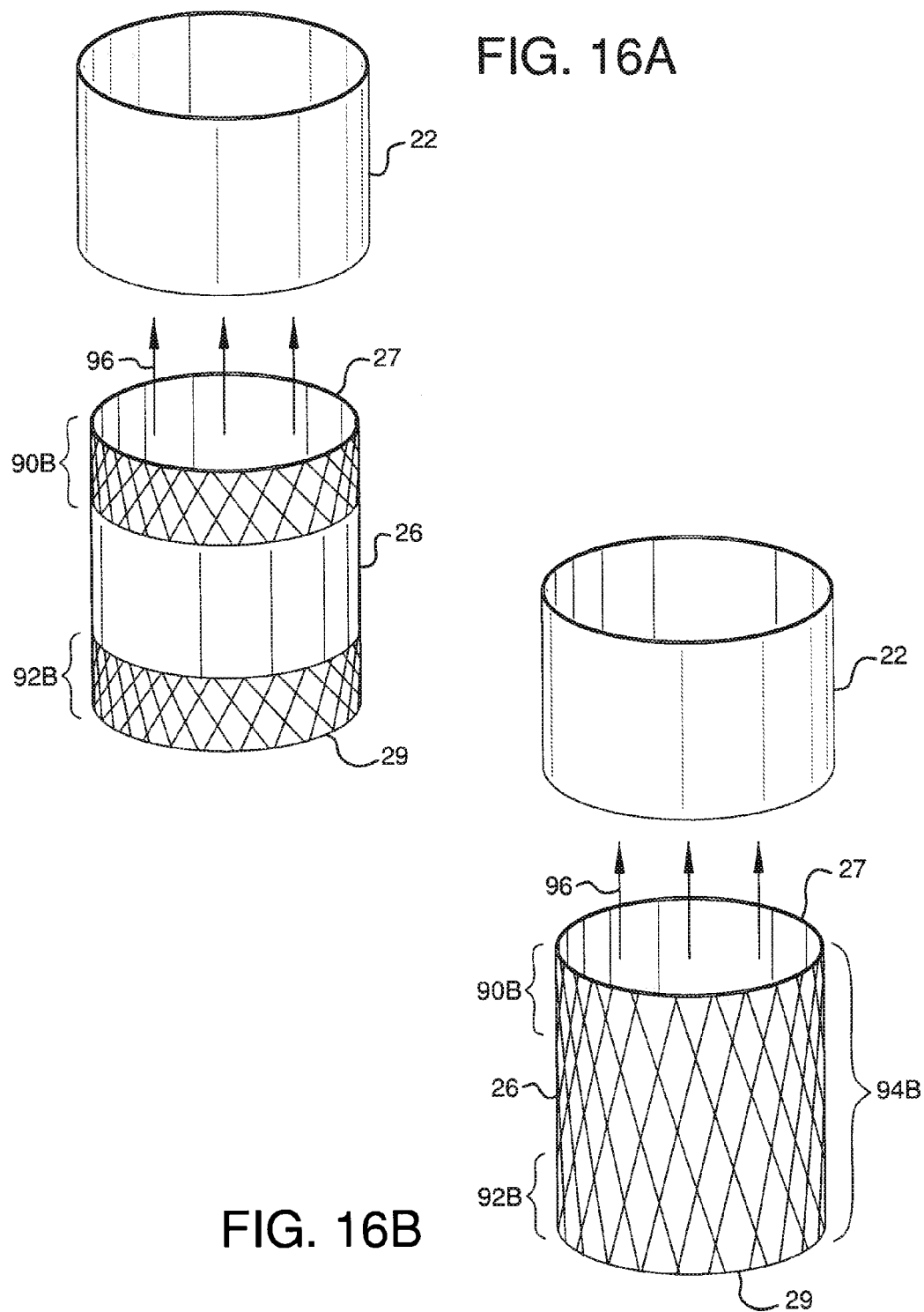

ENDOLUMINAL PROSTHETIC CONDUIT SYSTEMS AND METHOD OF COUPLING

CROSS REFERENCE TO RELATED APPLICATIONS

This application is a continuation of U.S. patent application Ser. No. 11/835,789, filed Aug. 8, 2007 now abandoned, which is incorporated by reference herein in its entirety for all purposes.

FIELD OF THE INVENTION

The present invention relates to endoluminal prosthetic conduit systems and in particular to methods and components for joining together endoluminal prosthetic conduit components.

BACKGROUND OF THE INVENTION

Stents or stent grafts are forms of transluminal prosthetic components which are used to maintain, open or dilate stenotic lesions in body lumens or to cover and repair an aneurysm. It is often the case that an aneurysm occurs at a branch or bifurcation in a vessel. To repair such an aneurysm using modular components, one current technique is to initially deploy across the aneurysm a main body stent or stent graft having a side wall opening. The side wall opening is aligned with the side branch ostium. A second stent or stent graft is then deployed through the main body stent side wall opening and into the side branch vessel. This modular repair approach requires the modular components to be effectively sealed at their connection points to prevent blood leakage into the aneurysm. In addition the modular components must be locked or joined together to prevent subsequent relative displacement of the modular components. Similar requirements apply to those procedures that use multiple stent grafts that are coupled together to increase the effective length of the repair device.

SUMMARY OF THE INVENTION

The present invention provides modular prosthetic conduit systems such as stent or stent graft systems. The modular prosthetic conduit systems may be tailored for the repair of aneurysms or for the repair of compromised vessel walls. The systems incorporate various embodiments for the secure interlocking of the multiple modular components used in a vessel repair procedure.

An aspect of the invention includes a prosthetic conduit system comprising: an expandable main conduit having a first open end, a second open end, a main conduit wall extending therebetween, an outer conduit surface, and an inner conduit surface having at least one protuberance thereon; an expandable secondary conduit having a first open end, a second open end, a secondary conduit wall extending therebetween, and an attachment portion extending at an angle of less than 90 degrees from the secondary conduit wall when in a deployed state; and wherein at least a portion of the secondary conduit is sized to fit inside the main conduit.

A further aspect of the invention includes a prosthetic conduit system comprising: an expandable main conduit having a first open end, a second open end, a main conduit wall extending therebetween, at least one opening through the main conduit wall, and an internal channel having an inner surface, an outer surface, a first open end located within the main conduit and a second open end at the opening in the main conduit wall; an expandable secondary conduit having a first open end, a second open end, a secondary conduit wall extending therebetween, and an attachment portion extending at an angle of less than 90 degrees from the secondary conduit wall when in a deployed state; and wherein at least a portion of the secondary conduit is sized to fit inside the internal channel and through the opening in the main conduit wall.

BRIEF DESCRIPTION OF THE DRAWINGS

FIGS. 16 A and 16B are side views of main conduits and secondary conduits according to certain aspects of the invention.

DETAILED DESCRIPTION OF THE INVENTION

A better understanding of the invention will be had with reference to the several figures.

Figure 1:
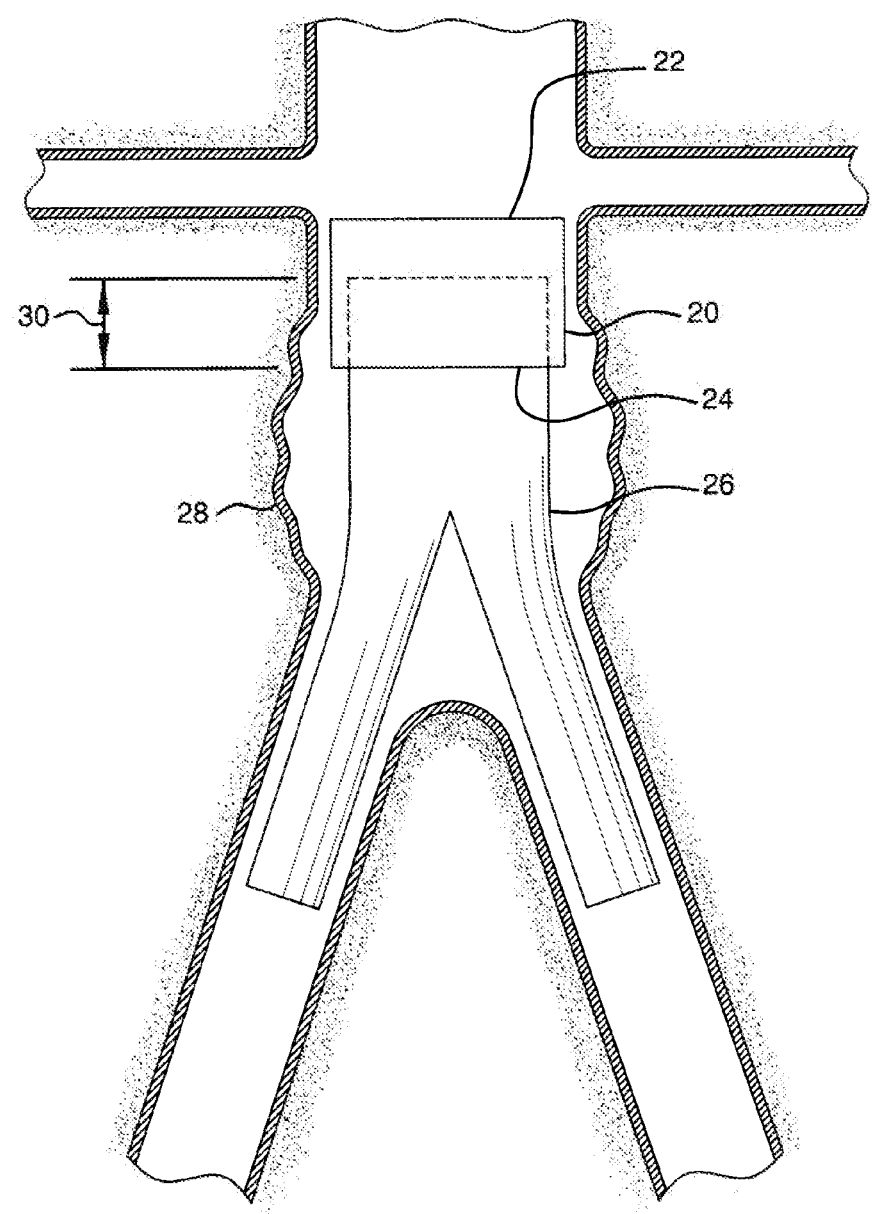
FIG. 1 is a side view of a main conduit with an interconnected secondary conduit as implanted across an aortic aneurysm.

Shown in FIG. 1 is a main conduit 20 having a first open end 22 and a second open end 24. A secondary conduit 26 is shown inserted into the second open end 24 of the main conduit 20. The secondary conduit 26 is shown as a bifurcated endoluminal device bridging an aortic aneurysm 28. The main conduit 20 and the secondary conduit 26 are expanded and share an engagement portion or engagement length 30. In an aspect of the invention the main conduit 20 and the secondary conduit 26 can be self-expanding or balloon expandable.

A main conduit can have various configurations including stent grafts with or without side-branches or side-branch openings. Stent grafts can be fabricated, for example, according to the methods and materials as generally disclosed in U.S. Pat. Nos. 6,042,605; 6,361,637; and 6,520,986 all to Martin et al. Details relating to the fabrication and materials used for a main conduit with an internal side branch support tube or channel can be found in, for example, U.S. Pat. No. 6,645,242 to Quinn.

Figure 2:
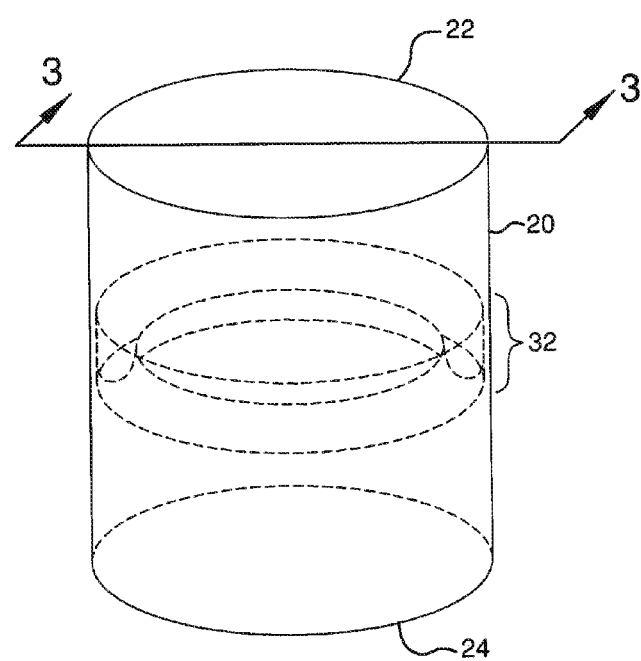
FIG. 2 is a perspective view of a main conduit having an internal protuberance.

The main conduit comprises at least one protuberance on the inner surface of the main conduit. Protuberances according to an aspect of the invention can be in many forms. For example, shown in FIG. 2 is a perspective view of a main conduit 20 having a first open end 22 and a second open end 24. Internal to the main conduit is protuberance in the form of cuff 32 on the inner surface of the main conduit.

Figure 3:
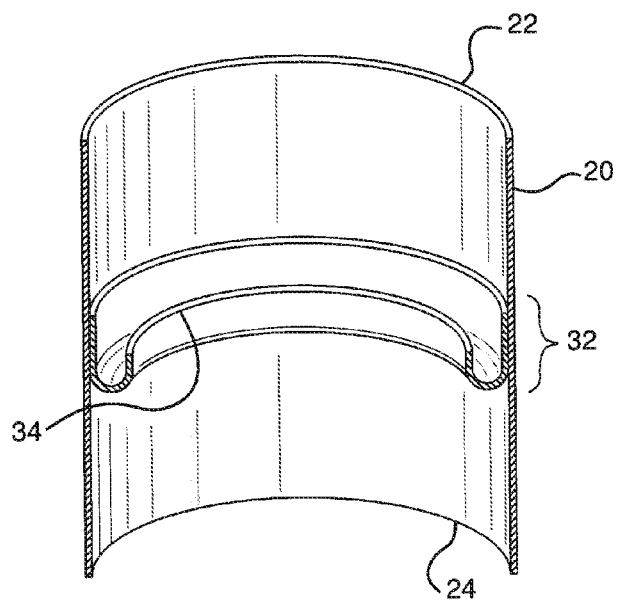
FIG. 3 is a cross-sectional view of a main conduit having an internal protuberance.

FIG. 3 is a cross-sectional view of a main conduit 20 as viewed along the cross-sectional plane 3 of FIG. 2. Shown is a section of a main conduit 20, first and second open ends 22, 24 and protuberance 32. The protuberance 32 is in the form of a cuff 34 that is configured to engage an attachment portion of a secondary conduit. A protuberance or cuff can have various configurations and can be fabricated, for example, from tubes, sheets or films formed into tubular shapes, woven or knitted fibers or ribbons or combinations thereof. Protuberance or cuff materials can include conventional medical grade materials such as nylon, polyester, polyethylene, polypropylene, polytetrafluoroethylene, polyvinylchloride, polyurethane and elastomeric organosilicon polymers. A protuberance or cuff can be joined to a graft or stent wall by sutures, medical grade adhesives or thermoplastics or can be integral to the graft or stent wall.

Figure 4:
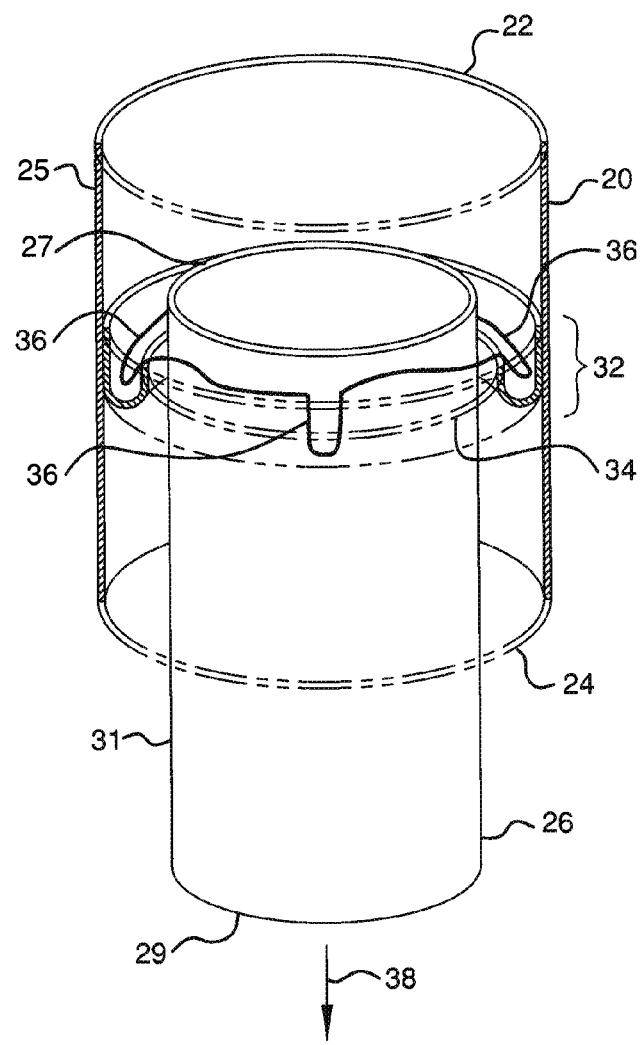
FIG. 4 is a perspective view of a main conduit joined to a secondary conduit.

Shown in FIG. 4 is a main conduit 20 having a first open end 22 and a second open end 24 and a wall 25 extending between the two open ends. The wall defines an outer conduit surface 21 and an inner conduit surface 23. A secondary conduit 26 is shown inserted into the second open end 24 of the main conduit 20. The secondary conduit 26 has a first open end 27 a second open end 29 and a wall 31 extending between the two open ends. The secondary conduit 26 has an attachment portion 36 shown in a deployed state as flared apices of a stent support structure. The attachment portion 36 is shown engaged into the protuberance 32 of main conduit 20. The flared apices of the stent support structure are therefore engaged and interlocked into the cuff 34, preventing or inhibiting the secondary conduit 26 from dislodging toward the direction indicated by arrow 38. An improved sealing surface between the secondary and the main conduits may also be provided by the protuberance 32. Forces exerted by the flow of blood may encourage or drive the flared apices of the stent support into contact with or full engagement with the cuff 34.

Figure 5A:
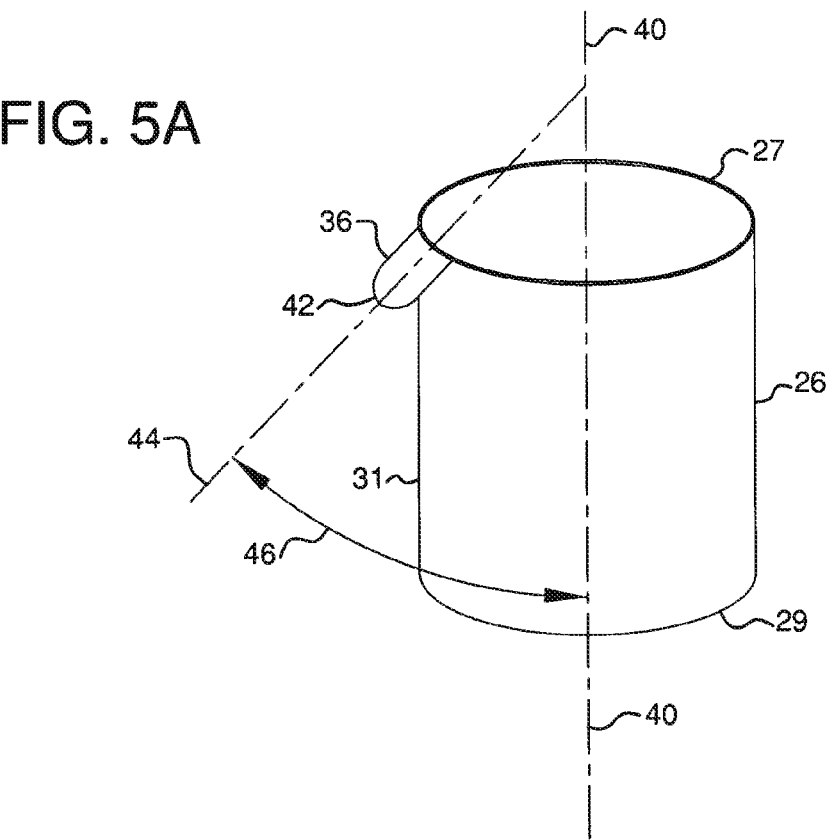
FIGS. 5A and 5B are perspective and side views of a secondary conduit having an attachment portion. Shown is a defined angle between an attachment portion and a secondary conduit longitudinal axis or secondary conduit wall.

Shown in FIG. 5A is a secondary conduit 26 having open ends 27 and 29, a wall 31 extending from open end 27 to open end 29, a longitudinal axis 40 and an attachment portion 36 shown in an unconstrained or deployed state as flared-out apices of a support stent. The inner surface 42 of the attachment portion 36 defines axis 44. An angle 46 is shown between the secondary conduit longitudinal axis 40 (and the wall 31) and the attachment portion axis 44. Shown is an angle of about 45°. Angle 46 can be any angle less than about 90°. For example angle 46 can be just less than 90°, about 80°, about 70°, about 60°, about 45°, about 30°, about 20° or less.

Figure 5B:
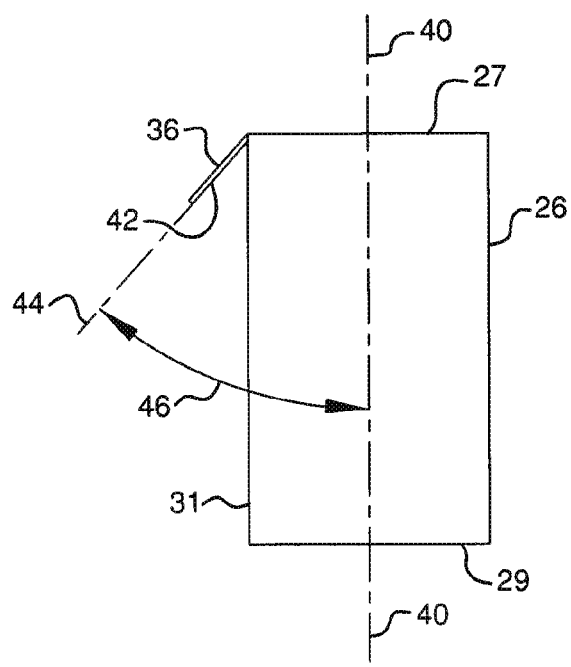

Similar to FIG. 5A, shown in FIG. 5B is a secondary conduit 26 having open ends 27 and 29, a wall 31 extending from open end 27 to open end 29, a longitudinal axis 40 and an attachment portion 36 shown in a deployed state as flared-out apices of a support stent. The inner surface 42 of the attachment portion 36 defines axis 44. An angle 46' is shown between the secondary conduit wall 31 and the attachment portion axis 44. Shown is an angle of about 45°.

Figure 6:
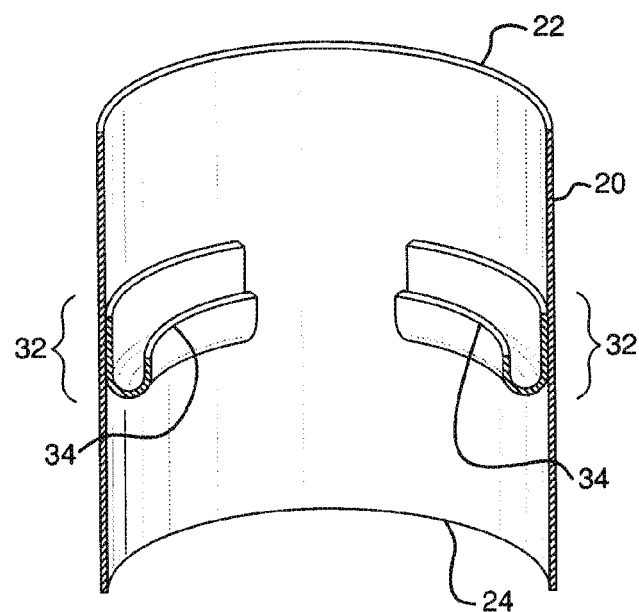
FIG. 6 is a cross-sectional view of a main conduit having an internal protuberance that is discontinuous or segmented.

Various alternate configurations of attachment portions and/or protuberances are possible. For example the protuberance 32 can be discontinuous, forming discrete protuberance segments along the inner wall of a main conduit. A main conduit can have two, three, four or five or more discrete protuberance segments, spaced along the inner wall. Shown in FIG. 6 is a cross-sectional view of a main conduit 20 as viewed along the cross-sectional plane 3 as defined in FIG. 2. Shown is a section of a main conduit 20, first and second open ends 22, 24 and discontinuous protuberances 34. The protuberances 34 form a series of cuffs that are configured to engage attachment portions of a secondary conduit, such as depicted in FIG. 4.

Figure 7:
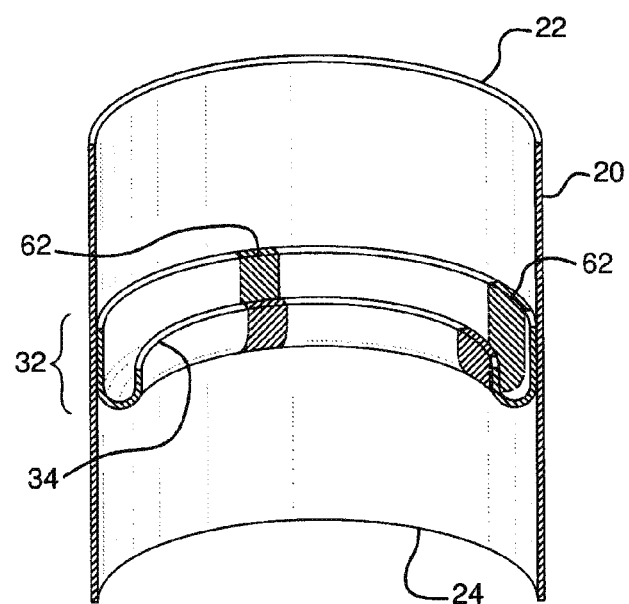
FIG. 7 is a cross-sectional view of a main conduit having an internal protuberance that incorporates stiffening support structures.

To assist in the engagement of an attachment portion, a protuberance can incorporate semi-rigid or densified segments along its length. Such semi-rigid sections along a protuberance may prevent or inhibit the protuberance from collapsing. Shown in FIG. 7 is a cross-sectional view of a main conduit 20 as viewed along the cross-sectional plane 3 as defined in FIG. 2. Shown is a section of a main conduit 20, first and second open ends 22, 24 and a protuberance, shown as cuff 34. Densified or semi-rigid sections 62 are incorporated into the protuberance to add rigidity to cuff 34 and thus inhibiting or even preventing the cuff from collapsing. Semi-rigid sections 62 can be incorporated into segmented or discontinuous protuberances as previously described in FIG. 6.

Semi-rigid or densified segments may be formed from conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as pericardium and collagen. Semi-rigid or densified segments can also comprise bioresorbable materials such as poly (amino acids), poly(anhydrides), poly(caprolactones), poly (lactic/glycolic acid) polymers, poly(hydroxybutyrates) and poly(orthoesters).

Figure 8:
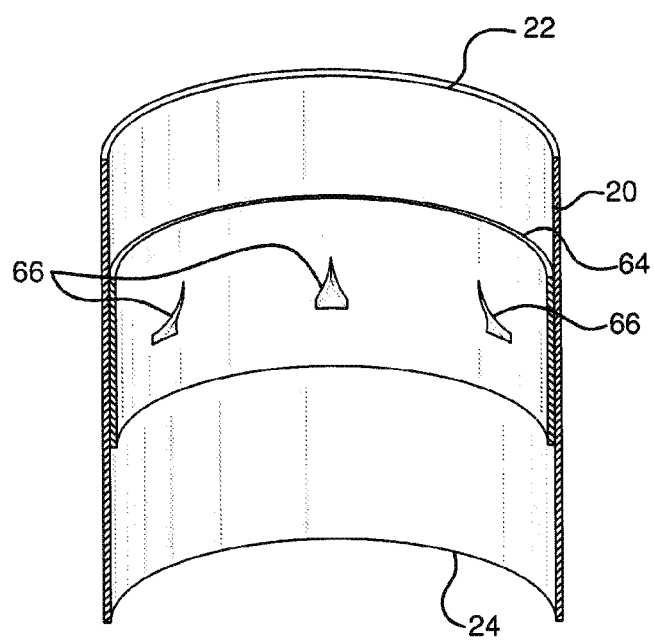
FIG. 8 is a cross-sectional view of a main conduit having an internal stent or support structure with barbs or hooks configured to engage a secondary conduit.

The at least one protuberance of the main conduit may comprise an internal stent or support structure that incorporates barbs, hooks or other suitable configurations to engage and/or lock with a secondary conduit. Shown in FIG. 8 is a cross-sectional view of a main conduit 20 as viewed along the cross-sectional plane 3 of FIG. 2. Shown is a section of a main conduit 20, first and second open ends 22, 24 and an internal stent or support structure 64. Protruding out of the stent or support structure 64 are a series of barbs or hooks 66. The barbs or hooks are oriented inwards toward the center of the main conduit and are configured to engage and/or lock onto a wall or attachment portion of a secondary conduit.

Figure 9A:
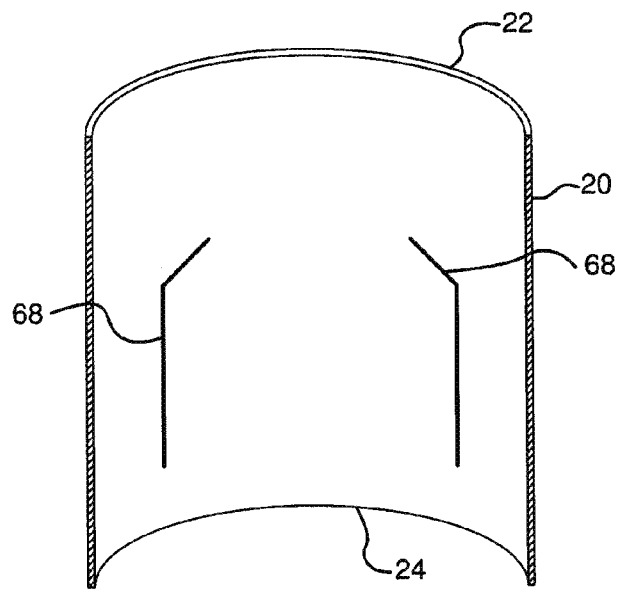
FIGS. 9A and 9B are cross-sectional views of a main conduit having internal barbs or internal hooks configured to engage a secondary conduit.
Figure 9B:
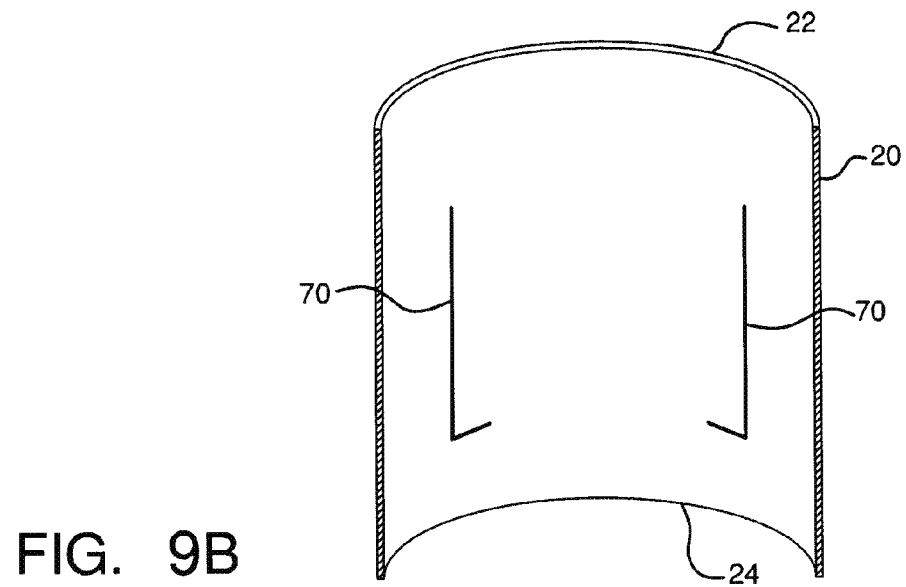

A main conduit may have a series of internal, barbs or hooks that are integral to the main conduit wall or integral to a main conduit support stent. For example if the main conduit has a stent support structure, portions of the stent can be formed into hooks or barbs that are configured to engage and lock a secondary conduit. Shown in FIG. 9A is a cross-sectional view of a main conduit 20 as viewed along the cross-sectional plane 3 of FIG. 2. Shown is a section of a main conduit 20, first and second open ends 22, 24 and a series of internal barbs 68. Similarly shown in FIG. 9B are a series of internal hooks 70. The barbs or hooks are oriented inwards toward the center of the main conduit and are configured to engage and/or lock onto an external wall of a secondary conduit. Barbs or hooks may be formed from conventional medical grade materials such as those listed above.

Figure 10A:
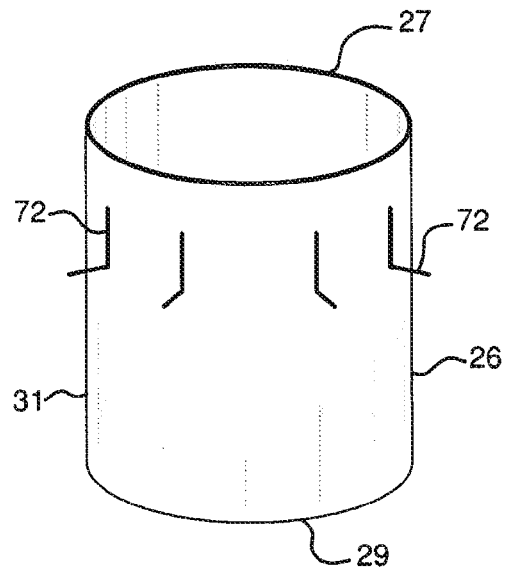
FIGS. 10A and 10B are perspective views of a secondary conduit having external barbs or external hooks configured to engage a main conduit.
Figure 10B:
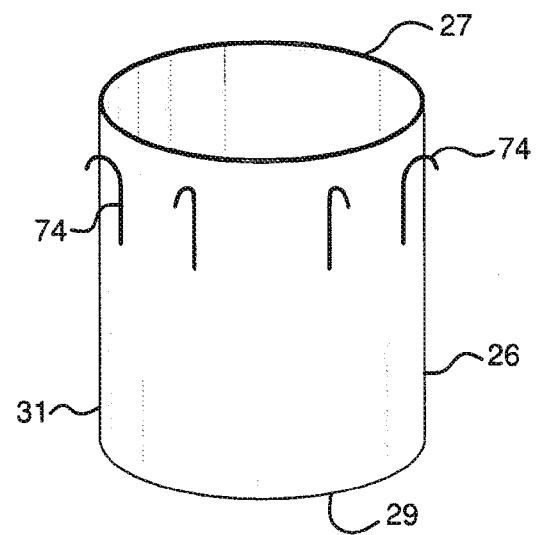

Secondary conduits can also incorporate various forms of attachment portions to engage and/or lock onto main conduits. For example shown in FIG. 10A is a perspective view of a secondary conduit 26 having first and second open ends 27, 29 and a wall 31. Protruding outwardly away from the secondary conduit wall 31 are a series of external barbs 72. Similarly, shown in FIG. 10B are a series of external hooks 74. The barbs or hooks are oriented outwardly away from the center of the secondary conduit and are configured to engage and lock onto an internal wall and/or protuberance of a main conduit.

Figure 11:
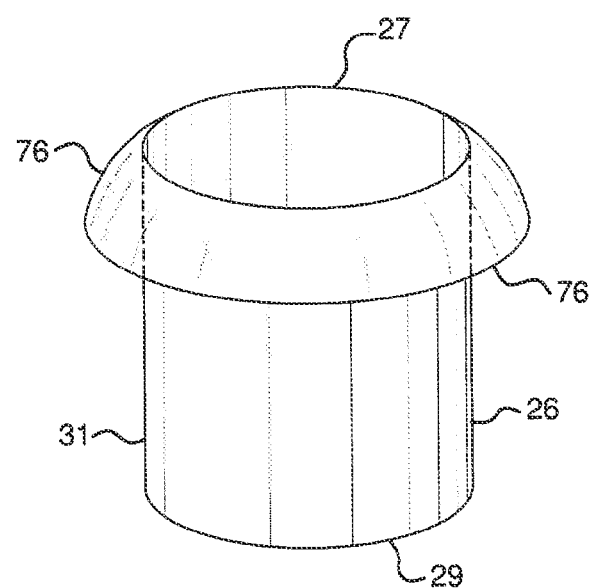
FIG. 11 is a perspective view of a secondary conduit having an external cuff that is configured to engage and lock onto an open end of a support channel.

A secondary conduit may also incorporate an external cuff that is configured to engage a main body protuberance or an open end of an internal channel. For example shown in FIG. 11 is a perspective view of a secondary conduit 26 having first and second open ends 27, 29 and a wall 31. Formed about the first open end 27 is an external cuff 76 configured to engage an internal protuberance or a first open end of an internal channel of a main conduit. The external cuff may incorporate semi-rigid sections as shown in FIG. 7 to add rigidity to the cuff.

Figure 12:
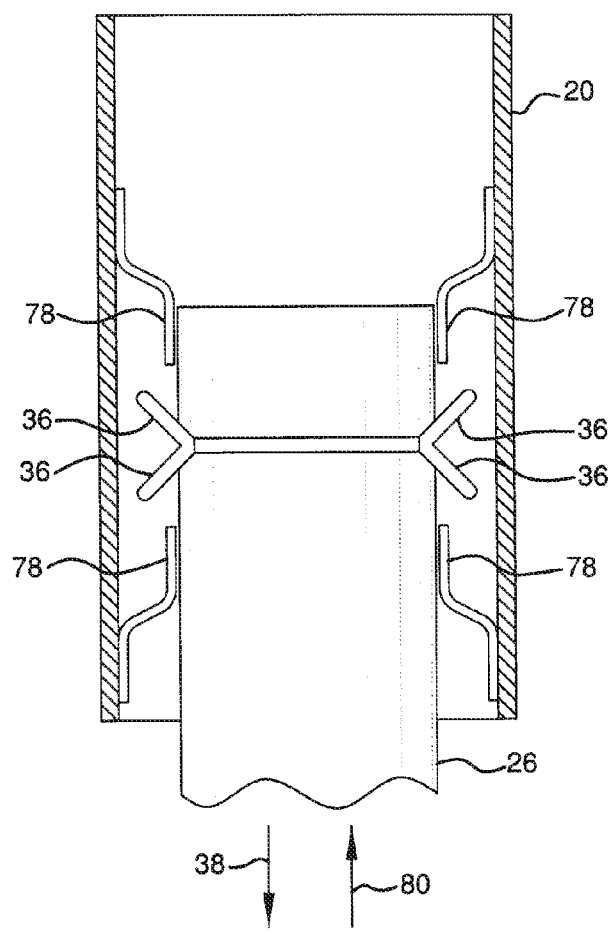
FIG. 12 is a cross-sectional view of a main conduit having two opposed cuffs.

A main conduit may have opposed anchoring cuffs that prevent a secondary conduit from being displaced in two directions. Shown in FIG. 12 is a cross-sectional view of a main conduit 20 having two opposed engagement cuffs 78. The cuffs 78 are configured in a linear state as shown in FIG. 2 and FIG. 3. The cuffs 78 are configured to engage attachment portions 36 of a secondary conduit 26. The engagement of the attachment portions 36 to the cuffs 78 inhibit or prevent dislodgement of the secondary conduit in the two directions shown by arrows 38 and 80.

Figure 13:
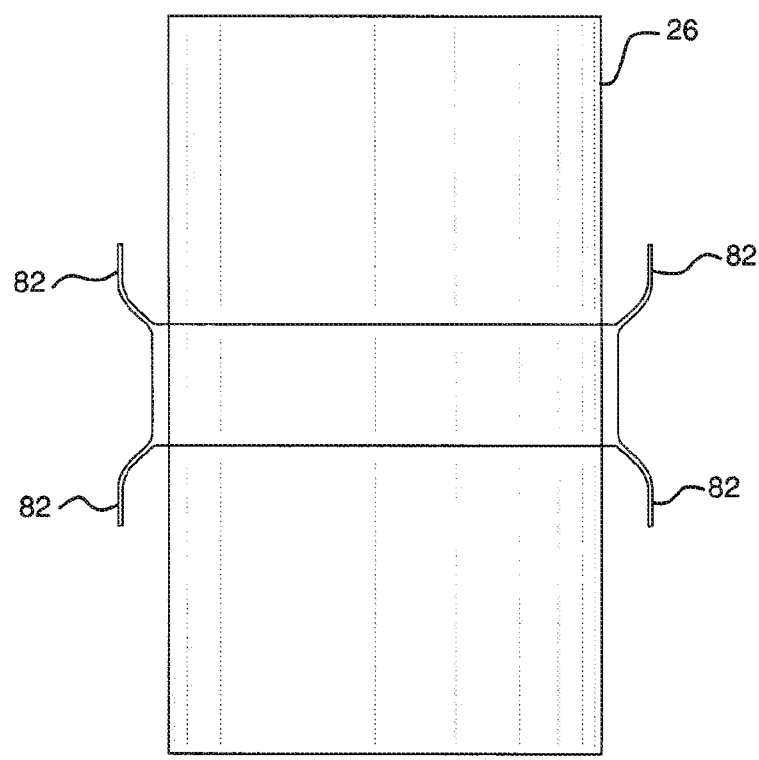
FIG. 13 is a side view of a secondary conduit having two opposed cuffs.

Secondary conduits can also incorporate attachment portions in the form of bi-directional cuffs that inhibit or prevent dislodgement in two directions. Shown in FIG. 13, is a secondary conduit 26 having bi-directional cuffs 82. The bi-directional cuffs 82 are configured to engage opposed main conduit cuffs as shown in FIG. 12.

In some surgical procedures it is desirable to have a side-branched endovascular device, particularly for the repair of a vessel that is in close proximity to branched vasculature.

Figure 14:
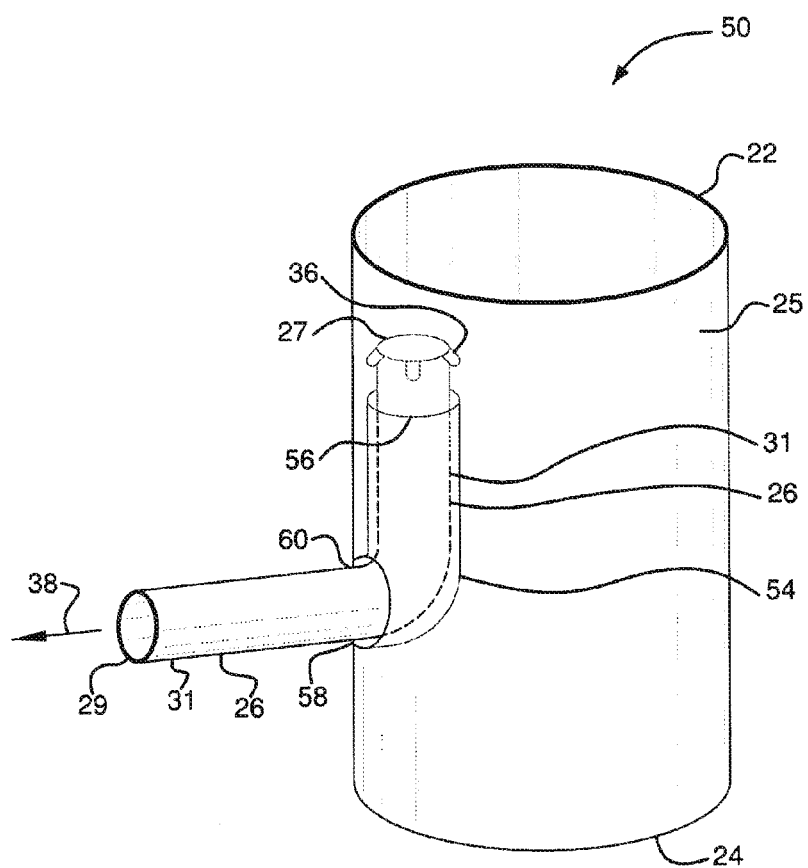
FIG. 14 is a perspective view of a main conduit and an interconnected secondary conduit.

FIG. 14 is a perspective view of an alternate main conduit 50 having a first open end 22 and a second open end 24. Within the main conduit 50 is an internal channel 54 having a first open end 56 and a second open end 58 that is aligned to an opening 60 in the main conduit wall 25. Such a main conduit can be fabricated according to the teaching in U.S. Pat. No. 6,645,242 to Quinn. A secondary conduit 26 having a first open end 27, a second open end 29, a wall 31, and an attachment portion 36 in a deployed state is shown inserted into the internal channel 54. The secondary conduit 26 is shown exiting out through the second open end 58 of the internal channel 54 and through the opening 60 in the main conduit wall. The attachment portion 36 is configured to engage and/or interlock onto the first open end 56 of the internal channel. This interlocking may prevent the dislodgement of the secondary conduit 26 along the direction depicted by arrow 38. Forces exerted by the flow of blood may encourage or drive the attachment portion 36 into full contact with the first open end 56 of the internal channel 54.

Stents can have various configurations as known in the art and can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Grafts can have various configurations as known in the art and can be fabricated, for example, from tubes, sheets or films formed into tubular shapes, woven or knitted fibers or ribbons or combinations thereof. Graft materials can include conventional medical grade materials such as nylon, polyester, polyethylene, polypropylene, polytetrafluoroethylene (including expanded polytetrafluoroethylene ("ePTFE")), polyvinylchloride, polyurethane and elastomeric organosilicon polymers.

Figure 15A:
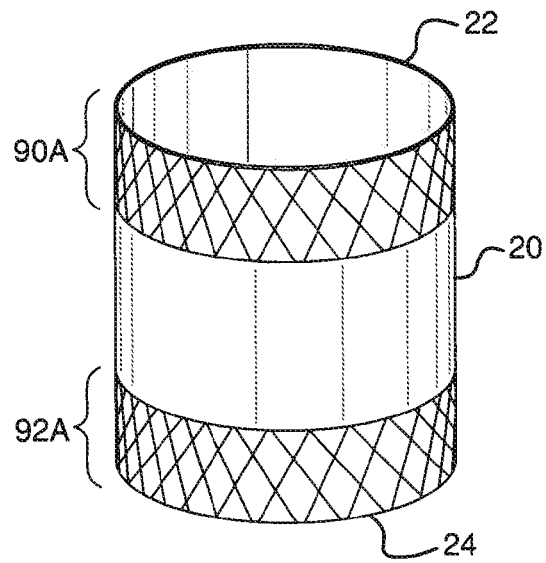
FIGS. 15 A and 15B are side views of main conduits according to certain aspects of the invention.
Figure 15B:
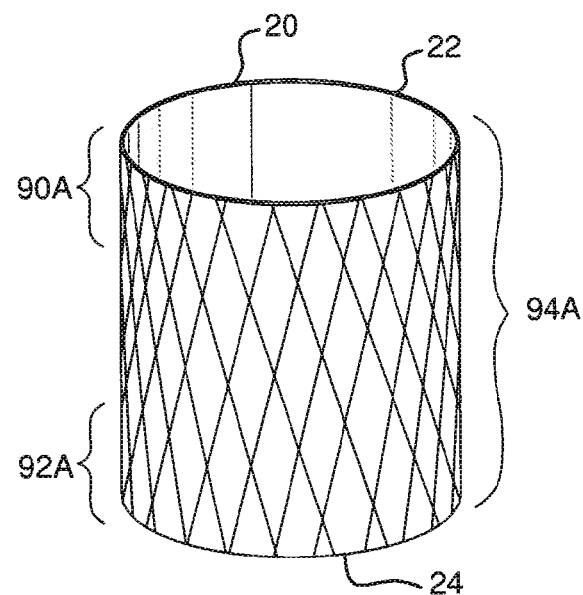

Stents can be used alone or in combination with graft materials. Stents can be configured on the external or internal surface of a graft or may be incorporated into the internal wall structure of a graft. Moreover, main and secondary conduits can incorporate various stent or support structures. For example as shown in FIG. 15A, a main conduit 20 may comprise separate stent segments 90A and 92A, positioned at or near the first and second open ends 22 and 24 of the main conduit 20. Similarly the stent segments 90A and 92A can comprise a single stent 94A extending from the first open end 22 to the second open end 24 of the main conduit 20.

Shown in FIGS. 16A and 16B are secondary conduits 26 tailored to be inserted into main conduits 22 along direction arrows 96. As shown in FIG. 16A, a secondary conduit 26 can incorporate stents 90B and 92B at or near the first and second open ends 27 and 29 of the secondary conduit 26. Similarly the stent segments 90B and 92B can comprise a single stent 94B extending from the first open end 27 to the second open end 29 of the secondary conduit 26.

Expandable conduits according to the invention can be delivered in a constrained state endoluminally by various catheter based procedures known in the art. For example self-expanding endoluminal devices can be loaded onto the distal end of a catheter, compressed and maintained in a constrained state by an external sheath. The sheath can be folded to form a tube positioned external to the compressed device. The sheath edges can be sewn together with a deployment cord that forms a "chain stitch". Once the constrained device is positioned at a target site within a vessel the device can be deployed. In the deployed state, the device may still be constrained by the vasculature or by another device. For example a device may assume a diameter of 20 mm when fully un-constrained. This same device may be deployed into a vessel (or other device) having a lumen diameter of 15 mm and would therefore be "constrained" in the deployed state. An "un-constrained state" can therefore be defined as the state assumed by the device when there are no external forces inhibiting the full expansion of the device. A "constrained state" can therefore be defined as the state assumed by the device in the presence of external forces that inhibit the full expansion of the device. The deployed state can be defined as the state assumed by the device when expanded into a vessel or other device.

To release and deploy the constrained device, one end of the deployment cord can be pulled to disrupt the chain stitch, allowing the sheath edges to separate and release the constrained device. Constraining sheaths and deployment cord stitching can be configured to release a self-expanding device in several ways. For example a constraining sheath may release a device starting from the proximal device end, terminating at the distal device end. In other configurations the device may be released starting from the distal end. Self expanding devices may also be released from the device center as the sheath disrupts towards the distal and proximal device ends. Details relating to constraining sheath materials, sheath methods of manufacture and main body compression techniques can be found in U.S. Pat. No. 6,352,561 to Leopold et al., and U.S. Pat. No. 6,551,350 Thornton et al.

In the deployment of a secondary conduit for example, the secondary conduit can be released from a constraining sheath starting at the proximal (or hub) end of the constrained conduit. In typical procedures, the attachment portion of the secondary conduit is located about the proximal end of the conduit and in an aspect of the invention this proximal end is the first end released from a constraining sheath, thus also deploying the attachment portion.

While particular embodiments of the present invention have been illustrated and described above, the present invention should not be limited to such particular illustrations and descriptions. It should be apparent that changes and modifications may be incorporated and embodied as part of the present invention within the scope of the following claims.

We claim:

1. Prosthetic conduit system comprising:
    an expandable main conduit having a first open end, a second open end, a main conduit wall extending therebetween, at least one opening through the main conduit wall, and an internal channel having an inner surface, an outer surface, a first open end located within the main conduit, and a second open end at the opening in the main conduit wall;
    an expandable secondary conduit extending through the internal channel and outwardly through the opening in the main conduit wall, the secondary conduit having a longitudinal axis extending between a first open end and a second open end of the secondary conduit, the secondary conduit having a secondary conduit wall extending between the first open end and the second open end of the secondary conduit, and an attachment portion extending outwardly at an angle of less than 90 degrees relative to the secondary conduit axis when in a deployed state and engaging a portion of the internal channel to constrain axial displacement of the secondary conduit relative to the main conduit,
    wherein the inner surface of the internal channel comprises at least one protuberance extending generally radially inwardly therefrom,
    wherein the attachment portion engages the protuberance on the inner surface of the internal channel to constrain axial displacement of the secondary conduit relative to the main conduit at least in a direction of blood flow therethrough.

2. The prosthetic conduit system of claim 1, wherein the at least one protuberance extends at an angle of less than 90 degrees relative to a longitudinal axis of the internal channel.

3. A prosthetic conduit system comprising:
    an expandable main conduit having a first open end, a second open end, a main conduit wall extending therebetween, at least one opening through the main conduit wall, and an internal channel having an inner surface, an outer surface, a first open end located within the main conduit, and a second open end at the opening in the main conduit wall;
    an expandable secondary conduit extending through the internal channel and outwardly through the opening in the main conduit wall, the secondary conduit having a longitudinal axis extending between a first open end and a second open end of the secondary conduit, the secondary conduit having a secondary conduit wall extending between the first open end and the second open end of the secondary conduit, and an attachment portion extending outwardly at an angle of less than 90 degrees relative to the secondary conduit axis when in a deployed state and engaging a portion of the internal channel to constrain axial displacement of the secondary conduit relative to the main conduit,
    wherein the attachment portion latchingly engages the first open end of the internal channel to constrain axial displacement of the secondary conduit relative to the main conduit at least in a direction of blood flow therethrough.

4. The prosthetic conduit system of claim 1, wherein the expandable main conduit is balloon expandable.

5. The prosthetic conduit system of claim 1, wherein the expandable main conduit is self-expanding.

6. The prosthetic conduit system of claim 1, wherein the at least one protuberance is selected from the group consisting of barbs, cuffs, hooks, flanges, stent apices and rings.

7. The prosthetic conduit system of claim 1, wherein the main conduit comprises a graft material.

8. The prosthetic conduit system of claim 1, wherein the secondary conduit comprises a graft material.

9. The prosthetic conduit system of claim 7, wherein the graft material comprises ePTFE.

10. The prosthetic conduit system of claim 8, wherein in the graft material comprises ePTFE.

11. The prosthetic conduit system of claim 1, wherein the expandable main conduit comprises a first stent segment at the first open end and a second stent segment at the second open end.

12. The prosthetic conduit system of claim 11, wherein the first stent segment and the second stent segment comprise a single stent extending from the first open end to the second open end.

13. The prosthetic conduit system of claim 1, wherein the attachment portion comprises a flange.

14. The prosthetic conduit system of claim 11, wherein at least one of the first stent segment and the second stent segment comprises nitinol.

15. The prosthetic conduit system of claim 1, wherein the expandable secondary conduit comprises a first stent segment at the first open end and a second stent segment at the second open end.

16. The prosthetic conduit system of claim 15, wherein the first stent segment and the second stent segment comprise a single stent extending from the first open end to the second open end.

17. The prosthetic conduit system of claim 16, wherein at least one of the first stent segment and the second stent segment comprises nitinol.

18. The prosthetic conduit system of claim 3, wherein the expandable main conduit is balloon expandable.

19. The prosthetic conduit system of claim 3, wherein the expandable main conduit is self-expanding.

20. The prosthetic conduit system of claim 3, wherein the at least one protuberance is selected from the group consisting of barbs, cuffs, hooks, flanges, stent apices and rings.

21. The prosthetic conduit system of claim 3, wherein the main conduit comprises a graft material.

22. The prosthetic conduit system of claim 3, wherein the secondary conduit comprises a graft material.

23. The prosthetic conduit system of claim 21, wherein the graft material comprises ePTFE.

24. The prosthetic conduit system of claim 22, wherein in the graft material comprises ePTFE.

25. The prosthetic conduit system of claim 3, wherein the expandable main conduit comprises a first stent segment at the first open end and a second stent segment at the second open end.

26. The prosthetic conduit system of claim 25, wherein the first stent segment and the second stent segment comprise a single stent extending from the first open end to the second open end.

27. The prosthetic conduit system of claim 3, wherein the attachment portion comprises a flange.

28. The prosthetic conduit system of claim 25, wherein at least one of the first stent segment and the second stent segment comprises nitinol.

29. The prosthetic conduit system of claim 3, wherein the expandable secondary conduit comprises a first stent segment at the first open end and a second stent segment at the second open end.

30. The prosthetic conduit system of claim 29, wherein the first stent segment and the second stent segment comprise a single stent extending from the first open end to the second open end.

31. The prosthetic conduit system of claim 30, wherein at least one of the first stent segment and the second stent segment comprises nitinol.

\* \* \* \* \*